(12) United States Patent
Toguchida et al.

(10) Patent No.: US 11,207,303 B2
(45) Date of Patent: Dec. 28, 2021

(54) THERAPEUTIC AGENT FOR FIBRODYSPLASIA OSSIFICANS PROGRESSIVA

(71) Applicants: Kyoto University, Kyoto (JP); Sumitomo Dainippon Pharma Co., Ltd., Osaka (JP)

(72) Inventors: Junya Toguchida, Kyoto (JP); Makoto Ikeya, Kyoto (JP); Akira Ohta, Kyoto (JP); Kyosuke Hino, Osaka (JP)

(73) Assignees: Kyoto University, Kyoto (JP); Sumitomo Dainippon Pharma Co., Ltd., Osaka (JP)

( * ) Notice: Subject to any disclaimer, the term of this patent is extended or adjusted under 35 U.S.C. 154(b) by 169 days.

(21) Appl. No.: 15/546,149

(22) PCT Filed: Jan. 25, 2016

(86) PCT No.: PCT/JP2016/051988
§ 371 (c)(1),
(2) Date: Jul. 25, 2017

(87) PCT Pub. No.: WO2016/121680
PCT Pub. Date: Aug. 4, 2016

(65) Prior Publication Data
US 2018/0353485 A1    Dec. 13, 2018

(30) Foreign Application Priority Data
Jan. 26, 2015    (JP) .............................. JP2015-012570

(51) Int. Cl.
*A61K 31/436*    (2006.01)
*A61P 19/08*    (2006.01)
*A61K 31/675*    (2006.01)

(52) U.S. Cl.
CPC .......... *A61K 31/436* (2013.01); *A61K 31/675* (2013.01); *A61P 19/08* (2018.01)

(58) Field of Classification Search
CPC ....................................................... A61P 19/08
See application file for complete search history.

(56) References Cited

FOREIGN PATENT DOCUMENTS

| JP | 2009-513522 A | 4/2009 |
| WO | 2005/005434 A1 | 1/2005 |
| WO | 2015/152183 A1 | 10/2015 |

OTHER PUBLICATIONS

Groppe, Functional Modeling of the ACVR1 (R206H) Mutation in FOP, Clinical Orthopaedics and Related Research, 2007, 462, pp. 87-92 (Year: 2007).*

(Continued)

*Primary Examiner* — Savitha M Rao
*Assistant Examiner* — Andrew P Lee
(74) *Attorney, Agent, or Firm* — Morgan, Lewis & Bockius LLP

(57) ABSTRACT

The present invention relates to a prophylactic or therapeutic agent for fibrodysplasia ossificans progressiva comprising as an active ingredient, at least one compound selected from the group consisting of rapamycin, temsirolimus, everolimus, ridaforolimus, TAFA93, umirolimus, olcorolimus, zotarolimus, and pharmaceutically acceptable salts thereof.

11 Claims, 2 Drawing Sheets

Specification includes a Sequence Listing.

(56) References Cited

OTHER PUBLICATIONS

Kaplan, Fibrodysplasia ossificans progressiva, Best Practice & Research Clinical Rheumatology, 2008, 22(1), pp. 191-205. (Year: 2008).*

Kitterman et al., "Iatrogenic Harm Caused by Diagnostic Errors in Fibrodysplasia Ossificans Progressiva," Pediatrics, 116: e654-e661 (2005).

Kaplan et al., "The Histopathology of Fibrodysplasia Ossificans Progressiva," The Journal of Bone and Joint Surgery, 75-A: 220-230 (1993).

Shore et al., "A recurrent mutation in the BMP type I receptor ACVR1 causes inherited and sporadic fibrodysplasia ossificans progressiva," Nature Genetics, 38: 525-527 (2006).

Fukuda et al., "Constitutively Activated ALK2 and Increased SMAD1/5 Cooperatively Induce Bone Morphogenetic Protein Signaling in Fibrodysplasia Ossificans Progressiva," The Journal of Biological Chemistry, 284: 7149-7156 (2009).

van Dinther et al., "ALK2 R206H Mutation Linked to Fibrodysplasia Ossificans Progressiva Confers Constitutive Activity to the BMP Type I Receptor and Sensitizes Mesenchymal Cells to BMP-Induced Osteoblast Differentiation and Bone Formation," Journal of Bone and Mineral Research, 25: 1208-1215 (2010).

ten Dijke et al., "Activin receptor-like kinases: a novel subclass of cell-surface receptors with predicted serine/threonine kinase activity," Oncogene, 8: 2879-2887 (1993).

Macias-Silva et al., "Specific Activation of Smad1 Signaling Pathways by the BMP7 Type I Receptor, ALK2," The Journal of Biological Chemistry, 273: 25628-25636 (1998).

Mohedas et al., "Development of an ALK2-Biased BMP Type I Receptor Kinase Inhibitor," American Chemical Society—Chemical Biology, 8: 1291-1302 (2013).

Engers et al., "Synthesis and structure-activity relationships of a novel and selective bone morphogenetic protein receptor (BMP) inhibitor derived from the pyrazolo[1.5-α]pyrimidine scaffold of Dorsomorphin: The discovery of ML347 as an ALK2 versus ALK3 selective MLPCN probe," Bioorganic & Medicinal Chemistry Letters, 23: 3248-3252 (2013).

Kaplan et al., "Restoration of normal BMP signaling levels and osteogenic differentiation in FOP mesenchymal progenitor cells by mutant allele-specific targeting," Gene Therapy, 19: 786-790 (2012).

Shimono et al., "Potent inhibition of heterotopic ossification by nuclear retinoic acid receptor-γ agonists," Nature Medicine, 17: 454-460 (2011).

Kaplan et al., "Hematopoietic Stem-Cell Contribution to Ectopic Skeletogenesis," The Journal of Bone and Joint Surgery, 89-A: 347-357 (2007).

Morelon et al., "Sirolimus: a new promising immunosuppressive drug. Towards a rationale for its use in renal transplantation," Nephrology Dialysis Transplantation, 16:18-20 (2001).

Relbo et al., "Everolimus and Cyclosporine Equally Improve QoL in De Novo Heart Transplanted Patients: The Results of Randomized Controlled Trial (Schedule Trial)," 32: S128 (2014).

Matsumoto et al., "Induced pluripotent stem cells from patients with human fibrodysplasia ossificans progressiva show increased mineralization and cartilage formation," Orphanet Journal of Rare Diseases, 8: 190 (2013).

Hamasaki et al., "Pathogenic Mutation of ALK2 Inhibits Induced Pluripotent Stem Cell Reprogramming and Maintenance: Mechanisms of Reprogramming and Strategy for Drug Identification," Stem Cells, 30: 2437-2449 (2012).

Mohedas et al., "Structure-Activity Relationship of 3,5-Diaryl-2-aminopyridine ALK2 Inhibitors Reveals Unaltered Binding Affinity for Fibrodysplasia Ossificans Progressiva Causing Mutants," Journal of Medicinal Chemistry, 57: 7900-7915 (2014).

Chaikuad et al., "Structure of the Bone Morphogenetic Protein Receptor ALK2 and Implications for Fibrodysplasia Ossificans Progressiva," The Journal of Biological Chemistry, 287: 36990-36998 (2012).

Kaplan et al., "A new era for fibrodysplasia ossificans progressiva: a druggable target for the second skeleton," Expert Opinion on Biological Therapy, 7: 705-712 (2007).

Bovero et al., "A very rare case of neoplasia with uncertain prognosis," Italian Journal of Medicine, 7: S2, 14 (2013).

Yang et al., "Inhibition of mTOR and HIF pathways diminishes chondro-osteogenesis and cell proliferation in chondroblastoma," Tumor Biology, 34: 3111-3119 (2013).

Yeh et al., "Rapamycin Inhibits BMP-7-Induced Osteogenic and Lipogenic Marker Expressions in Fetal Rat Calvarial Cells," Journal of Cellular Biochemistry, 114: 1760-1771 (2013).

International Search Report issued in corresponding International Patent Application No. PCT/JP2016/051988 dated Mar. 15, 2016.

International Preliminary Report on Patentability and Written Opinion issued in counterpart International Patent Application No. PCT/JP2016/051988 dated Aug. 10, 2017.

* cited by examiner

THERAPEUTIC AGENT FOR FIBRODYSPLASIA OSSIFICANS PROGRESSIVA

SEQUENCE LISTING SUBMISSION VIA EFS-WEB

A computer readable text file, entitled "SequenceListing.txt" created on or about Jul. 24, 2017, with a file size of about 28 kb contains the sequence listing for this application and is hereby incorporated by reference in its entirety.

TECHNICAL FIELD

The present invention relates to prophylactic and therapeutic agents for fibrodysplasia ossificans progressiva comprising as active ingredients, rapamycin and its analogs. More specifically, the present invention relates to a prophylactic agent and a preventive method as well as to a therapeutic agent and a treatment method for suppressing flare-ups and/or heterotopic ossification, which are the major symptoms of fibrodysplasia ossificans progressiva.

BACKGROUND ART

Fibrodysplasia ossificans progressiva (FOP) is a hereditary disorder characterized by the main symptoms of the swellings accompanied by inflammation or pain (also referred to as "flare-ups") and the aberrant formation and growth of cartilages or bones (also referred to as "heterotopic ossification." In typical patients with fibrodysplasia ossificans progressiva (FOP patients), the flare-ups develop during their childhoods or school ages and the heterotopic ossification forms as the flare-ups disappear. Also, from then the systemic fibrous tissues, such as skeletal muscles, fascias, tendons and ligaments, ossify progressively and heterotopically, and the contracture, deformation or mobility failure of joints occurs.

The characteristics of the heterotopic ossification in FOP reside in that the heterotopic ossification are rapidly induced by the destruction and regeneration of soft tissues such as muscles (Non Patent Literature 1). It has been reported that the heterotopic ossification seen in FOP patients involve a process so-called as endochondral ossification (or enchondral ossification) where cartilages are first formed and then are replaced by bones (Non Patent Literature 2).

CITATION LIST

Patent Literature

Patent Literature 1: WO2015/152183

Non Patent Literature

Non Patent Literature 1: Pediatrics, 2005, 116, e654-661
Non Patent Literature 2: J. Bone Joint Surg. Am., 1993, 75(2), 220-230
Non Patent Literature 3: Nat. Genet. 2006, 38, 525-527
Non Patent Literature 4: J. Biol. Chem. 2009, 284(11), 7149-7156
Non Patent Literature 5: J. Bone Miner. Res. 2010, 25(6), 1208-1215
Non Patent Literature 6: Oncogene 1993, 8(10), 2879-2887
Non Patent Literature 7: J. Biol. Chem. 1998, 273(40), 25628-25636
Non Patent Literature 8: ACS Chem. Biol., 2013, 8(6), 1291-1302
Non Patent Literature 9: Bioorg. Med. Chem. Lett., 2013, 23(11), 3248-3252
Non Patent Literature 10: Gene Ther, 2012, 19(7), 786-790
Non-patent Literature 11: Nat. Med., 2011, 17(4), 454-460

SUMMARY OF INVENTION

Problems to be Solved by the Invention

FOP is a genetic disorder of the autosomal dominant type. It has been reported that FOP is caused by mutations of activin A receptor type I (also referred to as ACVR1 or ALK2), which is one of the bone morphogenetic protein type I receptors (BMP receptors) (Non Patent Literature 3). ACVR1 is a serine/threonine kinase that transduces signals in cells as a BMP receptor. It has been reported that the mutated ACVR1 seen in the FOP patients transduces signals in a BMP-independent manner (Non Patent Literature 4 and 5) and that its reactivity toward BMP is enhanced as compared with the normal ACVR1 (wild-type ACVR1).

The TGF-β superfamily is comprised of diverse members in excess of 20 kinds and is broadly classified into BMP family and TGF-β family. For example, BMP-7 is one of cytokines that belong to the BMP family. BMP (Bone Morphogenetic Protein) forms complexes with two kinds of receptors, which are Type I and Type II transmembrane serine/threonine kinases, and thereby, transduces signals into cells. On the other hand, activin is a ligand that is classified in the TGF-β family and is a dimer formed of inhibin β chains. Similarly to BMP, activin also forms complexes with type I and type II receptors, and thereby, transduces signals into cells. However, it is known that activin and BMP differ from each other with respect to the receptor molecules that transduce signals.

The gene of ACVR1, which is one of BMP type I receptors, is a gene found as a result of having searched genes that have sequence homologies to human type II activin receptors as well as to nematode Daf-1. For this reason, ACVR1 is also referred to as activin receptor-like kinase 2 (Non Patent Literature 6). However, later analyses have shown that the physiological ligand for ACVR1 is a ligand of the BMP family, such as BMP-7, and that activin has no signal transducing activity mediated by ACVR1 (Non Patent Literature 7).

Presently, steroids, non-steroidal anti-inflammatory agents, bisphosphonates, and others are used for the therapy of FOP. However, there exists no therapeutic drug for which clear effectiveness of suppressing the progression of the heterotopic ossification has been confirmed.

As for the treatment method of FOP, compounds that inhibit the kinase activity of ACVR1 have been studied (Non Patent Literature 8 and 9). Among these compounds, there are some for which the action for suppressing the heterotopic ossification is confirmed in experiments using animal models that mimic an aspect of the FOP pathology.

Another finding has been reported that when the selective suppression of expression of the mutated ACVR1 seen in an FOP patient using the RNA interference technique suppressed the osteogenic differentiation of dental pulp stem cells of exfoliated deciduous teeth derived from the FOP patient (Non Patent Literature 10).

In experiments where an animal model that mimicked an aspect of the FOP pathology was used, retinoic acid receptor γ agonists have been shown to suppress heterotopic ossification. It has been reported that the retinoic acid receptor γ agonist reduces the overall amounts and phosphorylation of Smad proteins, which are the transcription factors activated by BMP receptors such as ACVR1, and thereby, manifests its action (Non Patent Literature 11).

As described above, any of the treatment methods that have been reported thus far is a method which is based on that the expression or the enzymatic activity of ACVR1 is suppressed or on that the signals of Smad as a substrate of ACVR1 are attenuated. On the other hand, it has been reported that the mutated ACVR1, which will cause FOP, has enhanced ability to transduce BMP signals as compared with the normal ACVR1 and transduces the signals in a BMP-independent manner (Non Patent Literature 4 and 5); however, the relation with the pathology of FOP is unclear.

As stated above, the mechanism of the onset of FOP has remained unelucidated and no drug has been found that is used for the suppression of the onset of FOP or the treatment of FOP.

The present invention has been made in consideration of the above-mentioned circumstances and aims at providing a prophylactic and/or therapeutic agent for fibrodysplasia ossificans progressiva.

Means for Solving the Problems

As a result of repeated diligent investigations, the present inventors found that according to the studies using FOP patient-derived cells, activin, which transduces signals mediated naturally by activin A receptor type IB (ACVR1B) but not by ACVR1, intracellularly transduces the signals through the mutated ACVR1 as observed in FOP patients and that this aberrant signaling is one cause for the ectopic chondrogenic induction and osteogenic induction which are observed in the FOP patients (Patent Literature 1). Namely, a phenomenon, which was different from the normal chondrogenic differentiation and specifically occurred in the pathology of FOP, could be reproduced by treating chondrogenic progenitor cells with activin. Thus, the compounds which suppress the chondrogenic differentiation in FOP, namely those which suppress the heterotopic ossification in FOP, were screened by comparing degree of chondrogenesis with or without compounds when FOP patient-derived cells were treated with activin and compounds. Consequently, it was found that rapamycin and analogs thereof suppressed the chondrogenic differentiation of the mesenchymal stem cell-like cells derived from iPS cells, which were established from FOP patients, namely suppressed the heterotopic ossification; and this led to the completion of the present invention.

Rapamycin is also referred to as sirolimus and is one of macrolide-type compounds, which is produced by one species of Actinomycetes. It is known that rapamycin or structural analogs thereof, such as everolimus and temsirolymus, inhibit the activity of mTOR (mammalian target of rapamycin or mechanistic target of rapamycin). mTOR is a serine/threonine kinase that bears a central role in regulating cell division, growth, survival and so on. It is known that rapamycin and structural analogs thereof have immunosuppressive activity, smooth muscle proliferation suppressive activity, or anticancer activity. However, their relation with FOP has not been known up to the present time and has been found by the present inventors for the first time.

Specifically, the present invention relates to what is described below.

[1] A prophylactic or therapeutic agent for fibrodysplasia ossificans progressiva comprising as an active ingredient, at least one compound selected from the group consisting of rapamycin, temsirolimus, everolimus, ridaforolimus, TAFA93, umirolimus, olcorolimus, zotarolimus, and pharmaceutically acceptable salts thereof.

[2] The prophylactic or therapeutic agent according to [1], comprising as the active ingredient, at least one compound selected from the group consisting of rapamycin, temsirolimus, everolimus, ridaforolimus, and pharmaceutically acceptable salts thereof.

[3] The prophylactic or therapeutic agent according to [1], wherein the active ingredient is rapamycin or a pharmaceutically acceptable salt thereof.

[4] The prophylactic or therapeutic agent according to [1], wherein the active ingredient is everolimus or a pharmaceutically acceptable salt thereof.

[5] The prophylactic or therapeutic agent according to any one of [1] to [4], which is for use in a patient having an amino acid mutation(s) in activin A receptor type I (ACVR1).

[6] The prophylactic or therapeutic agent according to [5], wherein the amino acid mutation(s) comprise an amino acid mutation in a GS domain or a kinase domain of ACVR1.

[7] The prophylactic or therapeutic agent according to [6], wherein the amino acid mutation(s) in the GS domain or the kinase domain comprise at least one amino acid mutation in the amino acid sequence as set forth in SEQ NO: 2, the amino acid mutation being selected from the group consisting of an amino acid mutation of the 196th amino acid residue being proline, an amino acid mutation of the 197th amino acid residue being leucine and of the 198th amino acid residue being deleted, an amino acid mutation of the 202nd amino acid residue being isoleucine, an amino acid mutation of the 206th amino acid residue being histidine, an amino acid mutation of the 207th amino acid residue being glutamic acid, an amino acid mutation of the 258th amino acid residue being glycine or serine, an amino acid mutation of the 325th amino acid residue being alanine, an amino acid mutation of the 328th amino acid residue being glutamic acid, arginine, or tryptophan, an amino acid mutation of the 356th amino acid residue being aspartic acid, and an amino acid mutation of the 375th amino acid residue being proline.

[8] The prophylactic or therapeutic agent according to [6], wherein the amino acid mutation(s) in the GS domain of ACVR1 comprise the amino acid mutation of the 206th amino acid residue in the amino acid sequence as set forth in SEQ NO: 2 being histidine.

[9] The prophylactic or therapeutic agent according to any one of [1] to [8], which is a medicament for avoiding or suppressing the onset of flare-ups or heterotopic ossification.

[10] The prophylactic or therapeutic agent according to any one of [1] to [8], which is a medicament for curing, improving or alleviating the symptom of flare-ups or heterotopic ossification, or suppressing the progression of the symptom of the flare-ups or the heterotopic ossification.

Furthermore, the present invention relates to what is described below.

[11] A method for preventing or treating fibrodysplasia ossificans progressiva comprising administering to a mammal, an effective dose of at least one compound selected from the group consisting of rapamycin, temsirolimus, everolimus, ridaforolimus, TAFA93, umirolimus, olcorolimus, zotarolimus, and pharmaceutically acceptable salts thereof.

[12] The method according to [11], wherein the prevention or treatment of fibrodysplasia ossificans progressiva is avoidance or suppression of the onset of flare-ups or heterotopic ossification.

[13] The method according to [11], wherein the prevention or treatment of fibrodysplasia ossificans progressiva is cure, improvement or alleviation of the symptom of flare-ups or heterotopic ossification, or suppression of the progression of the symptom of the flare-ups or the heterotopic ossification.
[14] The method according to [11] to [13], wherein the mammal is a human.
[15] At least one compound for use in the prevention or treatment of fibrodysplasia ossificans progressiva, the at least one compound being selected from the group consisting of rapamycin, temsirolimus, everolimus, ridaforolimus, TAFA93, umirolimus, olcorolimus, zotarolimus, and pharmaceutically acceptable salts thereof.
[16] The compound according to [15], wherein the prevention or treatment of fibrodysplasia ossificans progressiva is avoidance or suppression of the onset of flare-ups or heterotopic ossification.
[17] The compound according to [15], wherein the prevention or treatment of fibrodysplasia ossificans progressiva is cure, improvement or alleviation of the symptom of flare-ups or heterotopic ossification, or suppression of the progression of the symptom of the flare-ups or the heterotopic ossification.
[18] Use of at least one compound for the manufacture of a prophylactic or therapeutic agent for fibrodysplasia ossificans progressiva, the at least one compound being selected from the group consisting of rapamycin, temsirolimus, everolimus, ridaforolimus, TAFA93, umirolimus, olcorolimus, zotarolimus, and pharmaceutically acceptable salts thereof.
[19] The use according to [18], wherein the prophylactic or therapeutic agent for fibrodysplasia ossificans progressiva is a medicament for avoiding or suppressing the onset of flare-ups or heterotopic ossification.
[20] The use according to [18], wherein the prophylactic or therapeutic agent for fibrodysplasia ossificans progressiva is a medicament for curing, improving, or alleviating the symptom of flare-ups or heterotopic ossification, or suppressing the progression of the symptom of the flare-ups or the heterotopic ossification.

Effects of the Invention

According to the present invention, it will be possible to provide a prophylactic and/or therapeutic agent for fibrodysplasia ossificans progressiva.

EMBODIMENTS FOR CARRYING OUT THE INVENTION

Preferred embodiments of the present invention will be explained in detail hereafter. Nevertheless, the present invention is not to be limited to the embodiments below.
According to the present embodiment, the prophylactic or therapeutic agent for fibrodysplasia ossificans progressiva (referred to as "FOP prophylactic/therapeutic agent" in some cases hereafter) comprises as an active ingredient, at least one compound selected from the group consisting of rapamycin (also referred to as sirolimus), temsirolimus, everolimus, ridaforolimus (also referred to as deforolimus), TAFA93, zotarolimus, umirolimus, olcorolimus, and pharmaceutically acceptable salts thereof. As used herein, the term "comprises as an active ingredient" encompasses the cases of the FOP prophylactic/therapeutic agent where there are included not only the free forms of rapamycin and its analogs, but also the forms of pharmaceutically acceptable salts thereof or further the forms of pharmaceutically acceptable hydrates or solvates. One kind of the active ingredients may be used, or two or more kinds may be used in combination.

Fibrodysplasia ossificans progressiva (FOP) is a genetic disorder where typically the systemic connective tissues ossify progressively and heterotopically (heterotopic ossification) and the lowered mobility or the deformation of the limbs and the trunk occurs from the childhood. The heterotopic ossification is an ossification that is observed in a tissue where osteogenesis does not naturally occur. In FOP, the motor function is significantly impaired because the heterotopic ossification of the systemic connective tissues occurs progressively. The present inventors have found that activin binds to the mutated ACVR1, and thereby, allows signals to be transduced into cells and that this signaling is one cause for the ectopic chondrogenic induction and osteogenic induction which are observed in FOP patients. Further, it is known that even if activin binds to the wild-type ACVR1, it does not transduce downstream signals of ACVR1.

Based on the aforementioned findings, the present inventors have discovered that: the chondrogenic differentiation can be induced by treating the FOP patient-derived cells with activin; further, the compounds which suppress the chondrogenic differentiation in FOP, namely those which suppress the heterotopic ossification in FOP, can be evaluated by comparing degree of chondrogenesis with or without compounds when FOP patient-derived cells were treated with activin and compounds.

The FOP prophylactic/therapeutic agent is a medicament for suppressing flare-ups and/or heterotopic ossification as the main symptoms of FOP. The flare-ups refer to the swellings accompanied by inflammation or pain; and the heterotopic ossification refers to the aberrant formation and growth of cartilages or bones. The details of the mutated ACVR1 mentioned above will be described later.

The prevention of fibrodysplasia ossificans progressiva means that the onset of the flare-ups or the heterotopic ossification is avoided or suppressed. For example, the prevention is accomplished by the following treatments:
(1) The FOP prophylactic/therapeutic agent is administered routinely prior to the onset of the flare-ups or the heterotopic ossification;
(2) If the episodes for developing the flare-ups such as an injury or infection come out, the FOP prophylactic/therapeutic agent is administered to avoid or suppress the onset of the flare-ups; and
(3) When inflammation, pain, flare-ups or the like occurs, the FOP prophylactic/therapeutic agent is administered to avoid or suppress the onset of the heterotopic ossification.

The therapy of fibrodysplasia ossificans progressiva means the cure, improvement or alleviation of the symptoms of fibrodysplasia ossificans progressiva, or the suppression of the progression of the symptoms. For example, the items shown below are encompassed by the therapy.

(1) Suppression of the symptom of the flare-ups or reduction of the period during which the flare-ups are being developed.

(2) Suppression of the symptom of the heterotopic ossification after the onset of the flare-ups.

(3) Suppression of the symptom or the progression of the heterotopic ossification which normally have a progressive course.

Activin A receptor type I (ACVR1) is one of BMP type I receptors and is, for example, a receptor encoded by the nucleic acid sequence as set forth in NCBI Accession No: NM_001105 (SEQ ID NO:1) or NM_001111067 (SEQ ID NO:3), which is an isoform of the former. The amino acid sequence of ACVR1 is, for example, represented by the amino acid sequence as set forth in SEQ ID NO:2 or SEQ ID NO:4.

As a substance (active ingredient) for suppressing the chondrogenic differentiation in the FOP patient-derived cells, it is preferably selected from the group consisting of rapamycin/sirolimus [Rapamune (registered trademark) by Pfizer Inc. or RAPALIMUS (registered trademark) by Nobel Pharma Co. Ltd.] (U.S. Pat. Nos. 3,929,992 and 5,362,718) and analogs thereof. Examples of the rapamycin analog include temsirolimus/CCI779 [TORISEL (registered trademark) by Pfizer Inc.] (U.S. Pat. No. 5,362,718), everolimus/RAD001 [AFINITOR (registered trademark) and CERTICAN (registered trademark) by Novartis Pharma AG] (U.S. Pat. No. 5,665,772), ridaforolimus/deforolimus/AP-23573 (ARIAD Pharmaceuticals, Inc) (U.S. Pat. No. 7,091,213), TAFA93 (Aurinia Pharmaceuticals Inc; Atrium Medical Corporation), umirolimus (Biosensors International Ltd; Terumo Corporation), olcorolimus (Novartis Pharma AG), and zotarolimus/ABT578 (Abbott) (WO 99/15530). As is described in the aforementioned patent publications, the above-stated compounds may be extracted and purified from culture media of a species of Actinomycetes as in the case of rapamycin, may be produced according to normal methods in the field of organic synthetic chemistry, or may be obtained from marketed ones. As the substance for suppressing the chondrogenic differentiation in the FOP patient-derived cells, there are preferably mentioned rapamycin, temsirolimus, everolimus, and ridaforolimus; and there are particularly, preferably mentioned rapamycin and everolimus. Rapamycin and analogs thereof may be their pharmaceutically acceptable salts.

Examples of the pharmaceutically acceptable salts of rapamycin or its analog include salts with inorganic acids such as hydrochloric acid, hydrobromic acid, hydroiodic acid, nitric acid, sulfuric acid, and phosphoric acid; salts with organic acids such as acetic acid, fumaric acid, maleic acid, succinic acid, citric acid, tartaric acid, adipic acid, gluconic acid, glucoheptic acid, glucuronic acid, terephthalic acid, methane sulfonic acid, lactic acid, hippuric acid, 1,2-ethane disulfonic acid, isethionic acid, lactobionic acid, oleic acid, pamoic acid, polygalacturonic acid, stearic acid, tannic acid, trifluoromethane sulfonic acid, benzene sulfonic acid, p-toluene sulfonic acid, lauryl sulfate, methyl sulfate, naphthalene sulfonic acid, and sulfosalicylic acid; quaternary ammonium salts with methyl bromide, methyl iodide, or the like; and salts with halogen ions such as a bromine ion, a chlorine ion, and an iodide ion.

Rapamycin or an analog thereof, or their pharmaceutically acceptable salts may take the forms of hydrates or solvates. Examples of such a solvent include water and ethanol.

When geometric or optical isomers are present for rapamycin or an analog thereof, or their pharmaceutically acceptable salts, the isomers or their salts are also encompassed by the present invention. In addition, when proton tautomerism is present in rapamycin or an analog thereof, or their pharmaceutically acceptable salts, the tautomers or their salts are also encompassed by the present invention.

The FOP prophylactic/therapeutic agent can be administered orally or parenterally (e.g., intravenously, subcutaneously, locally, transrectally, transdermally, intrathecally, or nasally). Examples of the dosage form for oral administration include tablets, capsules, pills, granules, powders, liquid formulations, and suspensions. Examples of the dosage form for parenteral administration include injectable aqueous formulations, injectable oily formulations, ointments, creams, lotions, aerosols, suppositories, and plasters. These formulations can be prepared using technologies that are conventionally known and can contain non-toxic and inert carriers or additives that are normally used in the medicinal field.

As pharmaceutical carriers, there are used substances that are commonly used in the medicinal field and that do not react with active ingredients. For example, there are used adjuvants that are normally used in the field of formulation technologies of medicaments, which include excipients, binders, preservatives, oxidation stabilizers, disintegrators, lubricants, flavoring agents, and others. Specific examples of the pharmaceutical carriers that are normally used in the production of the tablet, capsule, granule, and powder include excipients such as lactose, corn starch, sucrose, mannitol, calcium sulfate and crystalline cellulose; disintegrators such as carmellose sodium, modified starch, and carmellose calcium; binders such as methylcellulose, gelatin, gum arabic, ethylcellulose, hydroxypropylcellulose, and polyvinylpyrrolidone; and lubricants such as light anhydrous silicic acid, magnesium stearate, talc and hydrogenated oil. The tablet may be coated according to a well-known method, using a coating agent such carnauba wax, hydroxypropyl methyl cellulose, macrogol, hydroxypropylmethyl phthalate, celluloseacetate phthalate, sucrose, titanium oxide, a sorbitan fatty acid ester, or calcium phosphate.

Specific examples of the base for the suppository include cacao butter, a glycerol ester of a saturated fatty acid, glycerogelatin, and macrogol. In producing a suppository, a surfactant, preservative and the like may be added if necessary.

The liquid formulation may normally be prepared by dissolving the active ingredient into injectable distilled water; and if necessary, a solubilizer, a buffer, a pH adjuster, a tonicity agent, a soothing agent, and a preservative may be added thereto.

In the present embodiment, the "effective dose" means an amount of a medicament or drug that induces in a tissue, system, animal or human, a biological or medicinal response which is required by researchers or physicians.

The effective dose of the active ingredient in the FOP prophylactic/therapeutic agent differs depending on the dosage form: Normally, it is preferably from 0.05 to 10% by mass, and more preferably from 0.1 to 5% by mass in the FOP prophylactic/therapeutic agent. When the FOP prophylactic/therapeutic agent is a liquid formulation, the molar concentration of the active ingredient is preferably from 0.1 to 100 mM, and more preferably from 0.5 to 50 mM.

In the present embodiment, the prophylactic or therapeutic agent is intended to encompass pharmaceutical products comprising the specific ingredients at the specific amounts and all pharmaceutical products resulting from combinations of the specific ingredients at the specific amounts directly or indirectly.

Further, the FOP prophylactic/therapeutic agent may be administered in combination with other medicaments that can be combined for use as long as the purpose of the present invention is not impaired. The FOP prophylactic/therapeutic agent and other combinable medicaments may be administered separately or may be administered together as a single pharmaceutical composition. The FOP prophylactic/therapeutic agent may be administered prior to, simultaneously with, or posterior to other combinable medicaments. Examples of other combinable medicaments with the FOP prophylactic/agent/therapeutic agent include an ACVR1 kinase inhibitor, a binding inhibitor that inhibits interaction between activin and ACVR1, an expression inhibitor that suppresses the expression of activin, a steroid, a non-steroidal anti-inflammatory agent, a bisphosphonate, and a retinoic acid receptor γ agonist. Examples of the binding inhibitor include an activin receptor, a modified form thereof, and polypeptide fragments having their partial sequences; follistatin, a follistatin-like protein, a modified form thereof, and polypeptide fragments having their partial sequences; an antibody against activin and an antibody fragment thereof; and inhibin and a modified form thereof. Examples of the expression inhibitor include nucleic acids that suppress the gene expression of activin such as an antisense oligonucleotide, siRNA, shRNA, miRNA, and ribozyme, against an activin gene.

Examples of the mammal that is the subject include a mouse, rat, guinea pig, hamster, rabbit, cat, dog, sheep, pig, cattle, horse, goat, monkey, and human. The FOP prophylactic/therapeutic agent according to the present embodiment is preferably used against humans.

When the FOP prophylactic/therapeutic agent is administered to a human, its unit dosage form is, for example, used such that the active ingredient is administered at from 0.01 to 1000 mg, preferably at from 0.1 to 100 mg, although it differs with respect to the purpose of administration, the method of administration, or the circumstances of the subject to be administered (i.e., sex, age, weight, disease condition, etc.). Further, in one embodiment, when administered to a human, it is daily used once per day such that the active ingredient is administered at from 0.01 to 1000 mg, preferably at from 0.1 to 100 mg, and more preferably at from 1 to 10 mg.

The FOP prophylactic/therapeutic agent is desirably used for patients with amino acid mutation(s) in ACVR1 (mutated ACVR1). The "mutated ACVR1" represents an receptor protein that comprises an amino acid sequence with one or two deleted or substituted amino acids in the amino acid sequence as set forth in SEQ ID NO:2 and that transduces downstream signals through binding with activin.

Examples of the above-mentioned amino acid mutation include those shown in Table 1 below. Here, the number of an amino acid residue (amino acid residue number) represents the number of the amino acid residue in the amino acid sequence as set forth in SEQ ID NO:2.

TABLE 1

| Abbreviation | Amino acid residue no. | Amino acid before mutation | Amino acid after mutation |
|---|---|---|---|
| L196P | 196 | Lue | Pro |
| PF197/198L | 197, 198 | Pro, Phe | Leu |
| R202I | 202 | Arg | Ile |
| R206H | 206 | Arg | His |
| Q207E | 207 | Gln | Glu |
| R258G | 258 | Arg | Gly |
| R258S | 258 | Arg | Ser |

TABLE 1-continued

| Abbreviation | Amino acid residue no. | Amino acid before mutation | Amino acid after mutation |
|---|---|---|---|
| G325A | 325 | Gly | Ala |
| G328E | 328 | Gly | Glu |
| G328R | 328 | Gly | Arg |
| G328W | 328 | Gly | Trp |
| G356D | 356 | Gly | Asp |
| R375P | 375 | Arg | Pro |

For example, Kaplan et al., Human Mutation, Vol. 30, No. 3, 379-390, 2009 describes a correlation diagram of the primary sequences of ACVR1 with its functional domains; according to the correlation diagram, it can be comprehended that the enumerated amino acid mutations above are located within the GS domain or the kinase domain. The "GS domain" represents a domain where glycine and serine are abundant in the amino acid sequence. The "kinase domain" represents a domain that is required for the manifestation of the kinase activity in the amino acid sequence.

Therefore, it is preferred that the above-mentioned amino acid mutation(s) comprise an amino acid mutation within the GS domain or the kinase domain in ACVR1. It is preferred that the mutation(s) within the GS domain or the kinase domain comprise at least one amino acid mutation in the amino acid sequence as set forth in SEQ ID NO:2 which is selected from the group consisting of an amino acid mutation of the 196th amino acid residue being proline, an amino acid mutation of the 197th amino acid residue being leucine and of the 198th amino acid residue being deleted, an amino acid mutation of the 202nd amino acid residue being isoleucine, an amino acid mutation of the 206th amino acid residue being histidine, an amino acid mutation of the 207th amino acid residue being glutamic acid, an amino acid mutation of the 258th amino acid residue being glycine or serine, an amino acid mutation of the 325th amino acid residue being alanine, an amino acid mutation of the 328th amino acid residue being glutamic acid, arginine or tryptophan, an amino acid mutation of the 356th amino acid residue being aspartic acid, and an amino acid mutation of the 375th amino acid residue being proline. It is more preferred that the amino acid mutation(s) within the GS domain comprise the amino acid mutation of the 206th amino acid residue being histidine in the amino acid sequence as set forth in SEQ ID NO:2. Namely, the FOP prophylactic/therapeutic agent is desirably used for patients having ACVR1 which comprises an amino acid mutation(s) within the GS domain or the kinase domain. Specifically, there are mentioned the patients having ACVR1 comprising the amino acid mutation(s) described in Table 1. Particularly, there is desirably used for the patients having ACVR1 of which the 206th amino acid residue is histidine in the amino acid sequence as set forth in SEQ ID NO:2.

In one embodiment, the present invention can also be comprehended as a method for preventing or treating fibrodysplasia ossificans progressiva comprising administering to a mammal, an effective dose of at least one compound selected from the group consisting of rapamycin, temsirolimus, everolimus, ridaforolimus, TAFA93, umirolimus, olcorolimus, zotarolimus, and pharmaceutically acceptable salts thereof. In one embodiment, the present invention can further be comprehended as at least one compound for use in the prevention or treatment of fibrodysplasia ossificans progressiva, the at least one compound being selected from the group consisting of rapamycin, temsirolimus, everolimus, ridaforolimus, TAFA93, umirolimus, olcorolimus, zotarolimus, and pharmaceutically acceptable salts thereof. In one embodiment, the present invention can still further be comprehended as use of at least one compound for the manufacture of a prophylactic or therapeutic agent for fibrodysplasia ossificans progressiva, the at least one compound being selected from the group consisting of rapamycin, temsirolimus, everolimus, ridaforolimus, TAFA93, umirolimus, olcorolimus, zotarolimus, and pharmaceutically acceptable salts thereof. Preferred forms in these respective embodiments have been as described above.

EXAMPLES

The present invention will be explained in detail by reciting examples shown below; however, the present invention is not to be limited to these in any way.

Example 1: Effects on the Differentiation Induction to Chondrocytes (Methods)

According to the method of Yamanaka et. al., (Cell, 2007, 131 (5), 8611-8672), iPS cells derived from a FOP patient (referred to as "patient-derived iPS cells" in some cases hereafter) were established. It was ascertained that the cells of this patient had a typical mutation in the ACVR1 gene which would cause FOP. This mutation is a mutation that replaces the 206th arginine residue into a histidine residue in the amino acid sequence of ACVR1 (the amino acid sequence as set forth in SEQ ID NO:2). In addition, with a view toward using as a control, the mutation of the ACVR1 gene described above was corrected to the normal type (the wild type) by the gene correction with a BAC (Bacterial Artificial Chromosome) knock-in vector, thus establishing corrected iPS cells which may be referred to as "gene-corrected (rescued) iPS cell clone" in some cases hereafter.

The patient-derived iPS cells were cultured on a Matrigel coated plate [manufactured by Becton, Dickinson and Company; trade name, Growth Factor Reduced (GFR) BD MATRIGEL (registered trademark)] in mTeSR1 (manufactured by STEMCELL Technologies Inc.) under a feeder-free condition for two days. Then, they were cultured under the feeder-free condition for additional one week and were differentiated into neural crest cells by using serum-free medium [F12 Nutrient Mixture (manufactured by Gibco)]/ Iscove's Modified Dulbecco's Medium (IMDM) (manufactured by Sigma-Aldrich Co. LLC)/0.5% bovine serum albumin (BSA) (manufactured by Sigma-Aldrich Co. LLC)/1% Chemically Defined Lipid (CD-Lipid)(manufactured by Gibco; trade name, Chemically Defined Lipid Concentrate)/ 15 µg/mL apo-transferrin (manufactured by Sigma-Aldrich Co. LLC; trade name, apo-Transferrin human)/7 µg/mL insulin (Wako Pure Chemical Industries, Co., Ltd.; trade name, Insulin, Human, recombinant)/0.45 mM 1-Thioglycerol (manufactured by Sigma-Aldrich Co. LLC) supplemented with 10 µM SB-431542 (manufactured by Selleck Chemicals) and 1 µM CHIR99021 (manufactured by Wako Pure Chemical Industries Co., Ltd.). Subsequently, the cells were labeled with anti-CD271-APC antibody [manufactured by Becton, Dickinson and Company; trade name, ALEXA FLUOR (registered trademark), 647 Mouse anti-Human CD271], and CD 271 positive cells were sorted by using BD FACSAriaII (manufactured by Becton, Dickinson and Company). The sorted cells were subcultured several times with an alpha Modified Eagle Minimum Essential Medium (αMEM) (manufacture by Nacalai Tesque, Inc.)/10% fetal bovine serum (FBS) (manufactured by Nichirei Biosciences Inc.)/5 ng/mL FGF-2 (manufactured by Wako Pure Chemical Industries Co., Ltd.), and thereby, were differentiated into mesenchymal stem cell-like cells, which were provided for use in the experiments below.

Figure 1:
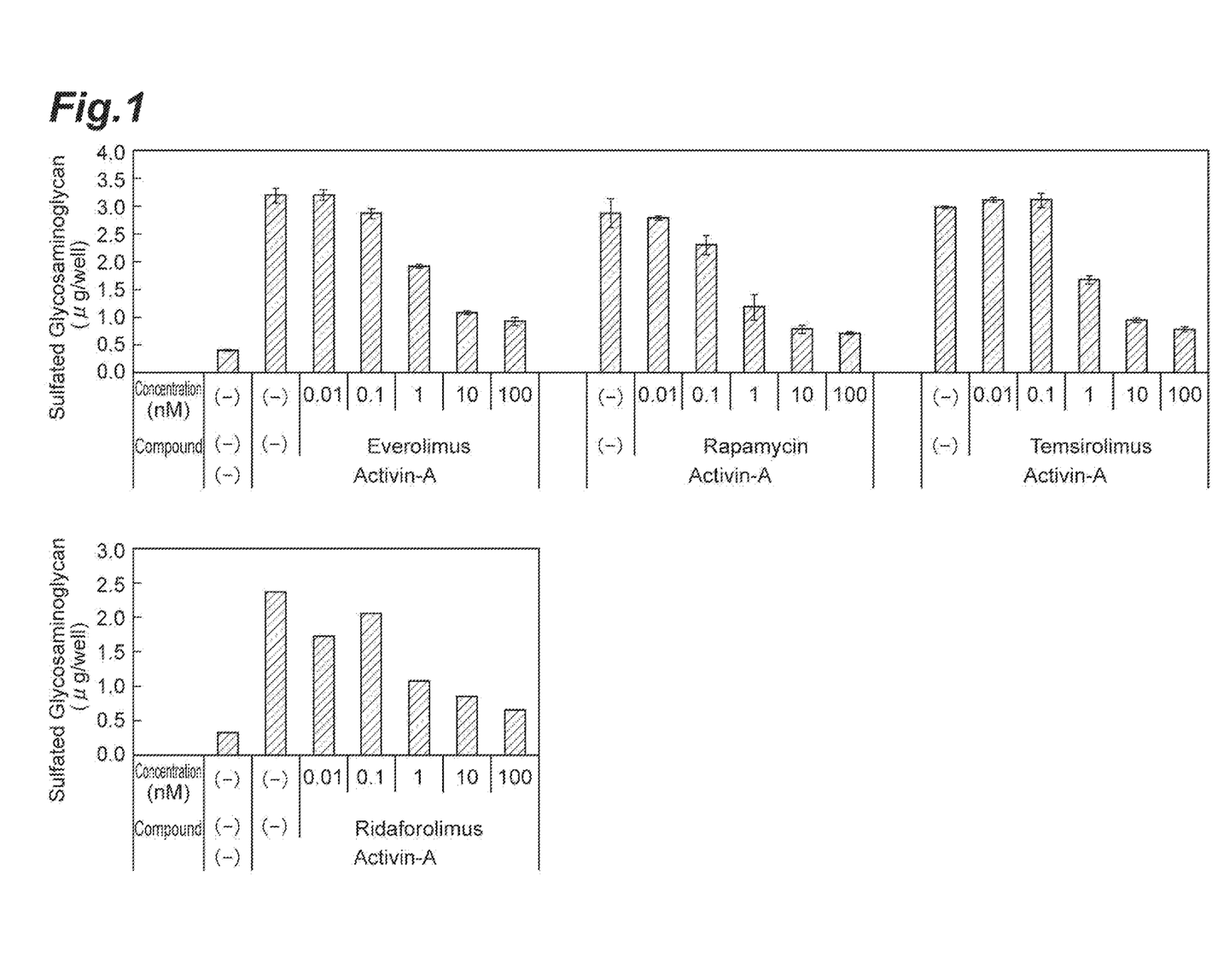
FIG. 1 is a graph showing amounts of sulfated glycosaminoglycan in chondrocytes differentiated from the FOP patient-derived cells.

These mesenchymal stem cell-like cells were cultured under a condition of a chondrogenic induction medium according to the method of Umeda (Sci. Rep, 2012, 2, 455) for six days and differentiated into chondrocytes. In the chondrogenic induction, 100 ng/mL human activin-A (manufactured by R&D Systems, Inc.; trade name, Recombinant Human/Mouse/Rat Activin A) and 1% FBS were allowed to coexist. Also, compounds for which their inhibitory effect against the chondrogenic differentiation were to be evaluated (concentrations of from 0.01 to 100 nM) were added simultaneously with human activin-A (referred to as "activin-A" in some cases hereafter). As the aforementioned compounds, there were used rapamycin (manufactured by Santa Cruz Biotechnology, Inc.), temsirolimus (manufactured by Sigma-Aldrich Co. LLC), everolimus (manufactured by Sigma-Aldrich Co. LLC), and ridaforolimus (manufactured by Selleck Chemicals). The degree of differentiation into chondrocytes was measured with a quantification kit for sulfated glycosaminoglycan (manufactured by Biocolor Inc.; trade name, Blyscan Glycosaminoglycan Assay Kit). Results are shown in FIG. 1. In FIG. 1, the bar graphs show the mean values±the standard deviations (SD) of each treatment group (n=3, provided that n=2 in the experiment of ridaforolimus).

(Results)

When the FOP patient-derived cells were treated with activin-A, the chondrogenic differentiation was promoted. It is revealed that rapamycin, temsirolimus, everolimus, and ridaforolimus suppressed the chondrogenic differentiation. $P<0.0001$ at 0.1, 1, 10, and 100 nM of rapamycin; at 1, 10, and 100 nM of everolimus or temsirolimus by Dunnett's multiple comparisons t-test compared to only human activin-A treatment group.

Example 2: In Vivo Evaluation of Rapamycin on Heterotopic Ossification Suppressing Action (Methods)

Figure 2:
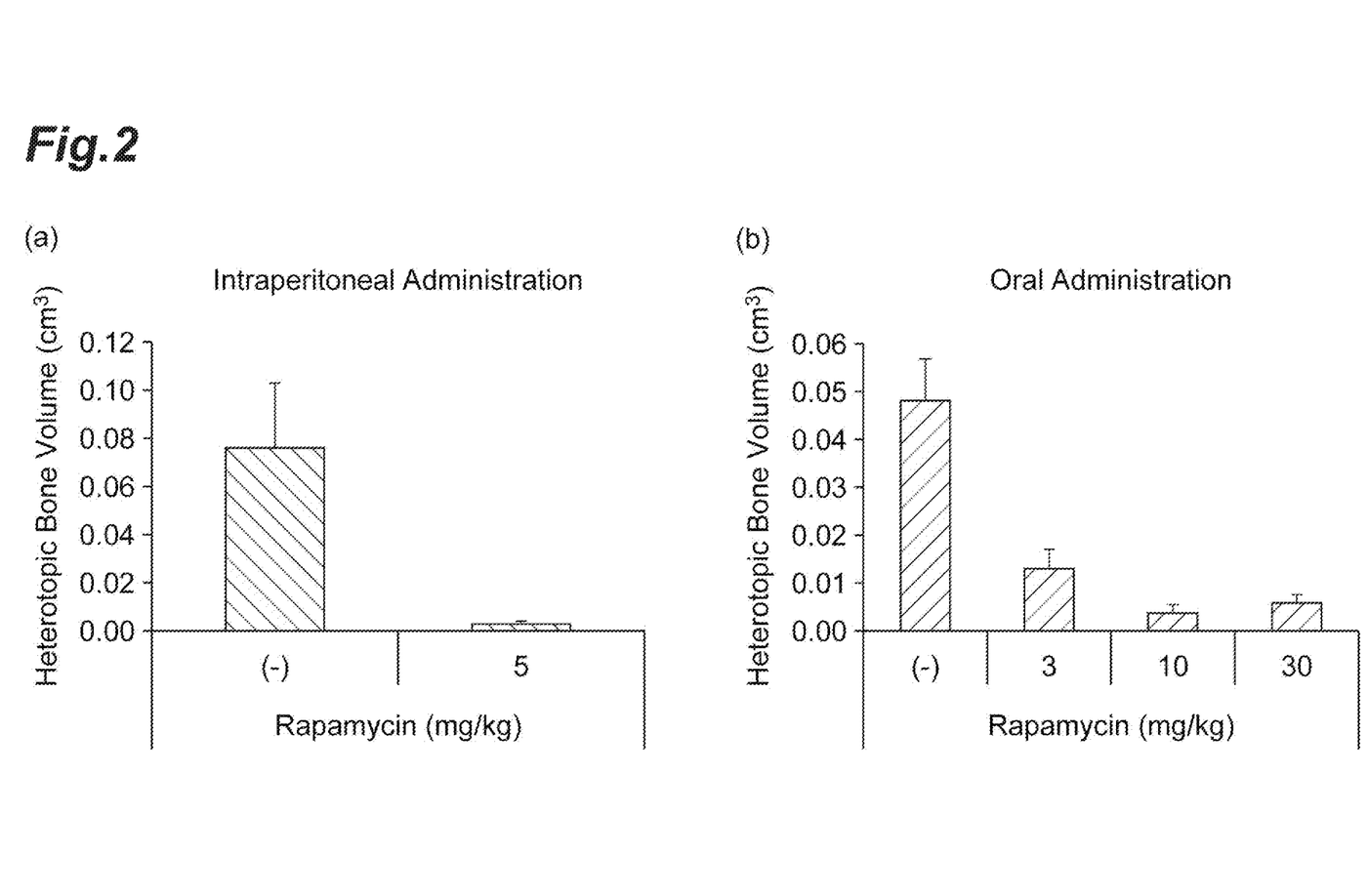
FIGS. 2(a) and 2(b) are graphs showing efficacies of rapamycin in mice model for human heterotopic ossification using the FOP patient-derived cells, where (a) is a graph in the case of intraperitoneal administration and (b) is a graph in the case of oral administration.

According to methods similarly to those of Example 1, mesenchymal stem cell-like cells were differentiated, respectively, from the patient-derived iPS cells and the gene-corrected (rescued) iPS cells. These cells and C3H10T1/2 cells expressing human activin-A were mixed and transplanted to immunodeficient mice (NOD/SCID mice), respectively. Specifically, a mixture of the mesenchymal stem cell-like cells differentiated from the patient-derived iPS cells and the C3H10T1/2 cells were transplanted to the right gastrocnemius muscle of the immunodeficient mice; and a mixture of the mesenchymal stem cell-like cells differentiated from the gene-corrected (rescued) iPS cells and the C3H10T1/2 cells were transplanted to the left gastrocnemius muscle of the immunodeficient mice. After the transplantation, rapamycin was administered orally (3, 10, or 30 mg/kg) or intraperitoneally (5 mg/kg) five times a week. Six weeks after the transplantation, a microCT scanner (trade name, inspeXio SMX-100CT; manufactured by Shimadzu Corporation) was used to observe the formation of heterotopic bones, and the heterotopic bone volume ($cm^3$) was calculated with TRI/3D-BON (manufactured by Ratoc System Engineering Co., Ltd.). The results of the calculated heterotopic bone volume formed in the right gastrocnemius muscle are shown in FIG. 2. In FIG. 2, the bar graphs show the mean values±the standard deviations (SD) of each administration group (n=4-5).

(Results)

In all the mice of the rapamycin non-administered group, the heterotopic ossification were observed at the sites (the right gastrocnemius muscle) where the mesenchymal stem cell-like cells differentiated from the patient-derived iPS cells and the C3H10T1/2 cells expressing human activin-A were transplanted. On the other hand, in the rapamycin administered group, the heterotopic ossification in the right gastrocnemius muscle were significantly suppressed. P<0.01 for the group where rapamycin was intraperitoneally administered at 5 mg/kg by Student's t-test compared to the rapamycin non-administered group; P<0.0001 for the group where rapamycin was orally administered at 3, 10, and 30 mg/kg by Dunnett's multiple comparisons t-test compared to the rapamycin non-administered group. Furthermore, in any of the groups, no heterotopic ossification was observed at the site (the left gastrocnemius muscle) where the mesenchymal stem cell-like cells differentiated from the gene-corrected (rescued) iPS cells and the C3H10T1/2 cells expressing human activin-A were transplanted.

INDUSTRIAL APPLICABILITY

FOP is a disorder for which no therapy with effectiveness that is clinically confirmed exists. The present invention provides an effective prophylactic/therapeutic agent for FOP that suppresses the flare-ups and/or the aberrant formation and growth of cartilages or bones, which are the main symptoms of FOP.

The invention claimed is:

1. A method for preventing or treating fibrodysplasia ossificans progressiva, comprising administering to a mammal, an effective dose of at least one compound selected from the group consisting of rapamycin, temsirolimus, everolimus, ridaforolimus, umirolimus, olcorolimus, zotarolimus, and pharmaceutically acceptable salts thereof.

2. The method according to claim 1, wherein the at least one compound is at least one compound selected from the group consisting of rapamycin, temsirolimus, everolimus, ridaforolimus, and pharmaceutically acceptable salts thereof.

3. The method according to claim 1, wherein the at least one compound is rapamycin or a pharmaceutically acceptable salt thereof.

4. The method according to claim 1, wherein the at least one compound is everolimus or a pharmaceutically acceptable salt thereof.

5. The method according to claim 1, wherein the prevention or treatment of fibrodysplasia ossificans progressiva is avoidance or suppression of the onset of flare-ups or heterotopic ossification.

6. The method according to claim 1, wherein the prevention or treatment of fibrodysplasia ossificans progressiva is cure, improvement or alleviation of the symptom of flare-ups or heterotopic ossification, or suppression of the progression of the symptom of the flare-ups or the heterotopic ossification.

7. The method according to claim 1, wherein the mammal is a human.

8. The method according to claim 7, wherein the human has one or more amino acid mutations in activin A receptor type I (ACVR1).

9. The method according to claim 8, wherein the one or more amino acid mutations comprise one or more amino acid mutations in a GS domain or a kinase domain of ACVR1.

10. The method according to claim 9, wherein
the one or more amino acid mutations in the GS domain or the kinase domain comprise at least one amino acid mutation in the amino acid sequence as set forth in SEQ NO: 2, the at least one amino acid mutation being selected from the group consisting of
an amino acid mutation of the 196th amino acid residue being proline, an amino acid mutation of the 197th amino acid residue being leucine and of the 198th amino acid residue being deleted, an amino acid mutation of the 202nd amino acid residue being isoleucine, an amino acid mutation of the 206th amino acid residue being histidine, an amino acid mutation of the 207th amino acid residue being glutamic acid, an amino acid mutation of the 258th amino acid residue being glycine or serine, an amino acid mutation of the 325th amino acid residue being alanine, an amino acid mutation of the 328th amino acid residue being glutamic acid, arginine, or tryptophan, an amino acid mutation of the 356th amino acid residue being aspartic acid, and an amino acid mutation of the 375th amino acid residue being proline.

11. The method according to claim 9, wherein the one or more amino acid mutations in the GS domain of ACVR1 comprise the amino acid mutation of the 206th amino acid residue in the amino acid sequence as set forth in SEQ NO: 2 being histidine.

* * * * *

SEQUENCE LISTING

```
<160> NUMBER OF SEQ ID NOS: 4

<210> SEQ ID NO 1
<211> LENGTH: 3062
<212> TYPE: DNA
<213> ORGANISM: Homo sapiens
<220> FEATURE:
<221> NAME/KEY: CDS
<222> LOCATION: (431)..(1960)

<400> SEQUENCE: 1
gaagagatgt gggcctctgg ggccgctgga ttcagtaact tccgtcgggt tctagactgg      60
ctcggctctg tccagtttgt gccagatagt ctcccacccc ctccccaccc ctcctttccc     120
ctggagattt gaacgctgct tgcatgggag aaaagctact tagagaagaa aacgttccac     180
ttagtaacag aagaaaagtc ttggttaaaa agttgtcatg aatttggctt ttggagagag     240
gcagcaagcc tggagcattg gtaagcgtca cactgccaaa gtgagagctg ctggagaact     300
cataatccca ggaacgcctc ttctactctc cgagtacccc agtgaccaga gtgagagaag     360
ctctgaacga gggcacgcgg cttgaaggac tgtgggcaga tgtgaccaag agcctgcatt     420
aagttgtaca atg gta gat gga gtg atg att ctt cct gtg ctt atc atg       469
            Met Val Asp Gly Val Met Ile Leu Pro Val Leu Ile Met
              1               5                   10 att gct ctc ccc tcc cct agt atg gaa gat gag aag ccc aag gtc aac       517
Ile Ala Leu Pro Ser Pro Ser Met Glu Asp Glu Lys Pro Lys Val Asn
     15                  20                  25 ccc aaa ctc tac atg tgt gtg tgt gaa ggt ctc tcc tgc ggt aat gag       565
Pro Lys Leu Tyr Met Cys Val Cys Glu Gly Leu Ser Cys Gly Asn Glu
 30              35                  40                  45 gac cac tgt gaa ggc cag cag tgc ttt tcc tca ctg agc atc aac gat       613
Asp His Cys Glu Gly Gln Gln Cys Phe Ser Ser Leu Ser Ile Asn Asp
             50                  55                  60 ggc ttc cac gtc tac cag aaa ggc tgc ttc cag gtt tat gag cag gga       661
Gly Phe His Val Tyr Gln Lys Gly Cys Phe Gln Val Tyr Glu Gln Gly
                 65                  70                  75 aag atg acc tgt aag acc ccg ccg tcc cct ggc caa gcc gtg gag tgc       709
Lys Met Thr Cys Lys Thr Pro Pro Ser Pro Gly Gln Ala Val Glu Cys
 80                  85                  90 tgc caa ggg gac tgg tgt aac agg aac atc acg gcc cag ctg ccc act       757
Cys Gln Gly Asp Trp Cys Asn Arg Asn Ile Thr Ala Gln Leu Pro Thr
     95                 100                 105 aaa gga aaa tcc ttc cct gga aca cag aat ttc cac ttg gag gtt ggc       805
Lys Gly Lys Ser Phe Pro Gly Thr Gln Asn Phe His Leu Glu Val Gly
110                 115                 120                 125
```

-continued

| | |
|---|---|
| ctc att att ctc tct gta gtg ttc gca gta tgt ctt tta gcc tgc ctg<br>Leu Ile Ile Leu Ser Val Val Phe Ala Val Cys Leu Leu Ala Cys Leu<br>130 135 140 | 853 |
| ctg gga gtt gct ctc cga aaa ttt aaa agg cgc aac caa gaa cgc ctc<br>Leu Gly Val Ala Leu Arg Lys Phe Lys Arg Arg Asn Gln Glu Arg Leu<br>145 150 155 | 901 |
| aat ccc cga gac gtg gag tat ggc act atc gaa ggg ctc atc acc acc<br>Asn Pro Arg Asp Val Glu Tyr Gly Thr Ile Glu Gly Leu Ile Thr Thr<br>160 165 170 | 949 |
| aat gtt gga gac agc act tta gca gat tta ttg gat cat tcg tgt aca<br>Asn Val Gly Asp Ser Thr Leu Ala Asp Leu Leu Asp His Ser Cys Thr<br>175 180 185 | 997 |
| tca gga agt ggc tct ggt ctt cct ttt ctg gta caa aga aca gtg gct<br>Ser Gly Ser Gly Ser Gly Leu Pro Phe Leu Val Gln Arg Thr Val Ala<br>190 195 200 205 | 1045 |
| cgc cag att aca ctg ttg gag tgt gtc ggg aaa ggc agg tat ggt gag<br>Arg Gln Ile Thr Leu Leu Glu Cys Val Gly Lys Gly Arg Tyr Gly Glu<br>210 215 220 | 1093 |
| gtg tgg agg ggc agc tgg caa ggg gag aat gtt gcc gtg aag atc ttc<br>Val Trp Arg Gly Ser Trp Gln Gly Glu Asn Val Ala Val Lys Ile Phe<br>225 230 235 | 1141 |
| tcc tcc cgt gat gag aag tca tgg ttc agg gaa acg gaa ttg tac aac<br>Ser Ser Arg Asp Glu Lys Ser Trp Phe Arg Glu Thr Glu Leu Tyr Asn<br>240 245 250 | 1189 |
| act gtg atg ctg agg cat gaa aat atc tta ggt ttc att gct tca gac<br>Thr Val Met Leu Arg His Glu Asn Ile Leu Gly Phe Ile Ala Ser Asp<br>255 260 265 | 1237 |
| atg aca tca aga cac tcc agt acc cag ctg tgg tta att aca cat tat<br>Met Thr Ser Arg His Ser Ser Thr Gln Leu Trp Leu Ile Thr His Tyr<br>270 275 280 285 | 1285 |
| cat gaa atg gga tcg ttg tac gac tat ctt cag ctt act act ctg gat<br>His Glu Met Gly Ser Leu Tyr Asp Tyr Leu Gln Leu Thr Thr Leu Asp<br>290 295 300 | 1333 |
| aca gtt agc tgc ctt cga ata gtg ctg tcc ata gct agt ggt ctt gca<br>Thr Val Ser Cys Leu Arg Ile Val Leu Ser Ile Ala Ser Gly Leu Ala<br>305 310 315 | 1381 |
| cat ttg cac ata gag ata ttt ggg acc caa ggg aaa cca gcc att gcc<br>His Leu His Ile Glu Ile Phe Gly Thr Gln Gly Lys Pro Ala Ile Ala<br>320 325 330 | 1429 |
| cat cga gat tta aag agc aaa aat att ctg gtt aag aag aat gga cag<br>His Arg Asp Leu Lys Ser Lys Asn Ile Leu Val Lys Lys Asn Gly Gln<br>335 340 345 | 1477 |
| tgt tgc ata gca gat ttg ggc ctg gca gtc atg cat tcc cag agc acc<br>Cys Cys Ile Ala Asp Leu Gly Leu Ala Val Met His Ser Gln Ser Thr<br>350 355 360 365 | 1525 |
| aat cag ctt gat gtg ggg aac aat ccc cgt gtg ggc acc aag cgc tac<br>Asn Gln Leu Asp Val Gly Asn Asn Pro Arg Val Gly Thr Lys Arg Tyr<br>370 375 380 | 1573 |
| atg gcc ccc gaa gtt cta gat gaa acc atc cag gtg gat tgt ttc gat<br>Met Ala Pro Glu Val Leu Asp Glu Thr Ile Gln Val Asp Cys Phe Asp<br>385 390 395 | 1621 |
| tct tat aaa agg gtc gat att tgg gcc ttt gga ctt gtt ttg tgg gaa<br>Ser Tyr Lys Arg Val Asp Ile Trp Ala Phe Gly Leu Val Leu Trp Glu<br>400 405 410 | 1669 |
| gtg gcc agg cgg atg gtg agc aat ggt ata gtg gag gat tac aag cca<br>Val Ala Arg Arg Met Val Ser Asn Gly Ile Val Glu Asp Tyr Lys Pro<br>415 420 425 | 1717 |
| ccg ttc tac gat gtg gtt ccc aat gac cca agt ttt gaa gat atg agg<br>Pro Phe Tyr Asp Val Val Pro Asn Asp Pro Ser Phe Glu Asp Met Arg<br>430 435 440 445 | 1765 |

| | | | | | | | | | | | | | | | | |
|---|---|---|---|---|---|---|---|---|---|---|---|---|---|---|---|---|
| aag | gta | gtc | tgt | gtg | gat | caa | caa | agg | cca | aac | ata | ccc | aac | aga | tgg | 1813 |
| Lys | Val | Val | Cys | Val | Asp | Gln | Gln | Arg | Pro | Asn | Ile | Pro | Asn | Arg | Trp | |
| | | | | 450 | | | | | 455 | | | | | 460 | | |
| ttc | tca | gac | ccg | aca | tta | acc | tct | ctg | gcc | aag | cta | atg | aaa | gaa | tgc | 1861 |
| Phe | Ser | Asp | Pro | Thr | Leu | Thr | Ser | Leu | Ala | Lys | Leu | Met | Lys | Glu | Cys | |
| | | | | 465 | | | | | 470 | | | | | 475 | | |
| tgg | tat | caa | aat | cca | tcc | gca | aga | ctc | aca | gca | ctg | cgt | atc | aaa | aag | 1909 |
| Trp | Tyr | Gln | Asn | Pro | Ser | Ala | Arg | Leu | Thr | Ala | Leu | Arg | Ile | Lys | Lys | |
| | | | 480 | | | | | 485 | | | | | 490 | | | |
| act | ttg | acc | aaa | att | gat | aat | tcc | ctc | gac | aaa | ttg | aaa | act | gac | tgt | 1957 |
| Thr | Leu | Thr | Lys | Ile | Asp | Asn | Ser | Leu | Asp | Lys | Leu | Lys | Thr | Asp | Cys | |
| | | | 495 | | | | | 500 | | | | | 505 | | | |

| | | |
|---|---|---|
| tga cattttcata gtgtcaagaa ggaagatttg acgttgttgt cattgtccag | 2010 |
| ctgggaccta atgctggcct gactggttgt cagaatggaa tccatctgtc tccctcccca | 2070 |
| aatggctgct tgacaaggc agacgtcgta cccagccatg tgttggggag acatcaaaac | 2130 |
| caccctaacc tcgctcgatg actgtgaact gggcatttca cgaactgttc acactgcaga | 2190 |
| gactaatgtt ggacagacac tgttgcaaag gtagggactg gaggaacaca gagaaatcct | 2250 |
| aaaagagatc tgggcattaa gtcagtggct ttgcatagct ttcacaagtc tcctagacac | 2310 |
| tccccacggg aaactcaagg aggtggtgaa ttttttaatca gcaatattgc ctgtgcttct | 2370 |
| cttctttatt gcactaggaa ttctttgcat tccttacttg cactgttact cttaattta | 2430 |
| aagacccaac ttgccaaaat gttggctgcg tactccactg gtctgtcttt ggataatagg | 2490 |
| aattcaattt ggcaaaacaa aatgtaatgt cagactttgc tgcattttac acatgtgctg | 2550 |
| atgtttacaa tgatgccgaa cattaggaat tgtttataca caactttgca aattattat | 2610 |
| tacttgtgca cttagtagtt tttacaaaac tgctttgtgc atatgttaaa gcttattttt | 2670 |
| atgtggtctt atgattttat tacagaaatg ttttttaacac tatactctaa aatggacatt | 2730 |
| ttcttttatt atcagttaaa atcacatttt aagtgcttca catttgtatg tgtgtagact | 2790 |
| gtaactttt ttcagttcat atgcagaacg tatttagcca ttacccacgt gacaccaccg | 2850 |
| aatatattac tgatttagaa gcaaagattt cagtagaatt ttagtcctga acgctacggg | 2910 |
| gaaaatgcat tttcttcaga attatccatt acgtgcattt aaactctgcc agaaaaaaat | 2970 |
| aactattttg ttttaatcta cttttttgtat ttagtagtta tttgtataaa ttaaataaac | 3030 |
| tgttttcaag tcaaaaaaaa aaaaaaaaaa aa | 3062 |

<210> SEQ ID NO 2
<211> LENGTH: 509
<212> TYPE: PRT
<213> ORGANISM: Homo sapiens

<400> SEQUENCE: 2

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
            85                  90                  95

```
Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
        130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
        210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
            275                 280                 285

Gly Ser Leu Tyr Asp Tyr Leu Gln Leu Thr Thr Leu Asp Thr Val Ser
        290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
            325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
        370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
            405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
            485                 490                 495

Lys Ile Asp Asn Ser Leu Asp Lys Leu Lys Thr Asp Cys
            500                 505
```

-continued

```
<210> SEQ ID NO 3
<211> LENGTH: 2881
<212> TYPE: DNA
<213> ORGANISM: Homo sapiens
<220> FEATURE:
<221> NAME/KEY: CDS
<222> LOCATION: (250)..(1779)

<400> SEQUENCE: 3
ctgcagcgcc cggctgcctc gcactccgcc tcccccggct cagccccggg ccgcggcggg      60
acccgagcct ggagcattgg taagcgtcac actgccaaag tgagagctgc tggagaactc     120
ataatcccag gaacgcctct tctactctcc gagtacccca gtgaccagag tgagagaagc     180
tctgaacgag ggcacgcggc ttgaaggact gtgggcagat gtgaccaaga gcctgcatta     240 agttgtaca atg gta gat gga gtg atg att ctt cct gtg ctt atc atg att     291
         Met Val Asp Gly Val Met Ile Leu Pro Val Leu Ile Met Ile
           1               5                  10 gct ctc ccc tcc cct agt atg gaa gat gag aag ccc aag gtc aac ccc       339
Ala Leu Pro Ser Pro Ser Met Glu Asp Glu Lys Pro Lys Val Asn Pro
 15              20                  25                  30 aaa ctc tac atg tgt gtg tgt gaa ggc ctc tcc tgc ggt aat gag gac       387
Lys Leu Tyr Met Cys Val Cys Glu Gly Leu Ser Cys Gly Asn Glu Asp
             35                  40                  45 cac tgt gaa ggc cag cag tgc ttt tcc tca ctg agc atc aac gat ggc       435
His Cys Glu Gly Gln Gln Cys Phe Ser Ser Leu Ser Ile Asn Asp Gly
         50                  55                  60 ttc cac gtc tac cag aaa ggc tgc ttc cag gtt tat gag cag gga aag       483
Phe His Val Tyr Gln Lys Gly Cys Phe Gln Val Tyr Glu Gln Gly Lys
     65                  70                  75 atg acc tgt aag acc ccg ccg tcc cct ggc caa gcc gtg gag tgc tgc       531
Met Thr Cys Lys Thr Pro Pro Ser Pro Gly Gln Ala Val Glu Cys Cys
 80                  85                  90 caa ggg gac tgg tgt aac agg aac atc acg gcc cag ctg ccc act aaa       579
Gln Gly Asp Trp Cys Asn Arg Asn Ile Thr Ala Gln Leu Pro Thr Lys
 95                 100                 105                 110 gga aaa tcc ttc cct gga aca cag aat ttc cac ttg gag gtt ggc ctc       627
Gly Lys Ser Phe Pro Gly Thr Gln Asn Phe His Leu Glu Val Gly Leu
                115                 120                 125 att att ctc tct gta gtg ttc gca gta tgt ctt tta gcc tgc ctg ctg       675
Ile Ile Leu Ser Val Val Phe Ala Val Cys Leu Leu Ala Cys Leu Leu
            130                 135                 140 gga gtt gct ctc cga aaa ttt aaa agg cgc aac caa gaa cgc ctc aat       723
Gly Val Ala Leu Arg Lys Phe Lys Arg Arg Asn Gln Glu Arg Leu Asn
        145                 150                 155 ccc cga gac gtg gag tat ggc act atc gaa ggg ctc atc acc acc aat       771
Pro Arg Asp Val Glu Tyr Gly Thr Ile Glu Gly Leu Ile Thr Thr Asn
    160                 165                 170 gtt gga gac agc act tta gca gat tta ttg gat cat tcg tgt aca tca       819
Val Gly Asp Ser Thr Leu Ala Asp Leu Leu Asp His Ser Cys Thr Ser
175                 180                 185                 190 gga agt ggc tct ggt ctt cct ttt ctg gta caa aga aca gtg gct cgc       867
Gly Ser Gly Ser Gly Leu Pro Phe Leu Val Gln Arg Thr Val Ala Arg
                195                 200                 205 cag att aca ctg ttg gag tgt gtc ggg aaa ggc agg tat ggt gag gtg       915
Gln Ile Thr Leu Leu Glu Cys Val Gly Lys Gly Arg Tyr Gly Glu Val
            210                 215                 220 tgg agg ggc agc tgg caa ggg gag aat gtt gcc gtg aag atc ttc tcc       963
Trp Arg Gly Ser Trp Gln Gly Glu Asn Val Ala Val Lys Ile Phe Ser
        225                 230                 235
```

```
tcc cgt gat gag aag tca tgg ttc agg gaa acg gaa ttg tac aac act     1011
Ser Arg Asp Glu Lys Ser Trp Phe Arg Glu Thr Glu Leu Tyr Asn Thr
    240             245             250 gtg atg ctg agg cat gaa aat atc tta ggt ttc att gct tca gac atg     1059
Val Met Leu Arg His Glu Asn Ile Leu Gly Phe Ile Ala Ser Asp Met
255             260             265             270 aca tca aga cac tcc agt acc cag ctg tgg tta att aca cat tat cat     1107
Thr Ser Arg His Ser Ser Thr Gln Leu Trp Leu Ile Thr His Tyr His
            275             280             285 gaa atg gga tcg ttg tac gac tat ctt cag ctt act act ctg gat aca     1155
Glu Met Gly Ser Leu Tyr Asp Tyr Leu Gln Leu Thr Thr Leu Asp Thr
        290             295             300 gtt agc tgc ctt cga ata gtg ctg tcc ata gct agt ggt ctt gca cat     1203
Val Ser Cys Leu Arg Ile Val Leu Ser Ile Ala Ser Gly Leu Ala His
    305             310             315 ttg cac ata gag ata ttt ggg acc caa ggg aaa cca gcc att gcc cat     1251
Leu His Ile Glu Ile Phe Gly Thr Gln Gly Lys Pro Ala Ile Ala His
320             325             330 cga gat tta aag agc aaa aat att ctg gtt aag aag aat gga cag tgt     1299
Arg Asp Leu Lys Ser Lys Asn Ile Leu Val Lys Lys Asn Gly Gln Cys
335             340             345             350 tgc ata gca gat ttg ggc ctg gca gtc atg cat tcc cag agc acc aat     1347
Cys Ile Ala Asp Leu Gly Leu Ala Val Met His Ser Gln Ser Thr Asn
            355             360             365 cag ctt gat gtg ggg aac aat ccc cgt gtg ggc acc aag cgc tac atg     1395
Gln Leu Asp Val Gly Asn Asn Pro Arg Val Gly Thr Lys Arg Tyr Met
        370             375             380 gcc ccc gaa gtt cta gat gaa acc atc cag gtg gat tgt ttc gat tct     1443
Ala Pro Glu Val Leu Asp Glu Thr Ile Gln Val Asp Cys Phe Asp Ser
    385             390             395 tat aaa agg gtc gat att tgg gcc ttt gga ctt gtt tgt tgg gaa gtg     1491
Tyr Lys Arg Val Asp Ile Trp Ala Phe Gly Leu Val Leu Trp Glu Val
400             405             410 gcc agg cgg atg gtg agc aat ggt ata gtg gag gat tac aag cca ccg     1539
Ala Arg Arg Met Val Ser Asn Gly Ile Val Glu Asp Tyr Lys Pro Pro
415             420             425             430 ttc tac gat gtg gtt ccc aat gac cca agt ttt gaa gat atg agg aag     1587
Phe Tyr Asp Val Val Pro Asn Asp Pro Ser Phe Glu Asp Met Arg Lys
            435             440             445 gta gtc tgt gtg gat caa caa agg cca aac ata ccc aac aga tgg ttc     1635
Val Val Cys Val Asp Gln Gln Arg Pro Asn Ile Pro Asn Arg Trp Phe
        450             455             460 tca gac ccg aca tta acc tct ctg gcc aag cta atg aaa gaa tgc tgg     1683
Ser Asp Pro Thr Leu Thr Ser Leu Ala Lys Leu Met Lys Glu Cys Trp
    465             470             475 tat caa aat cca tcc gca aga ctc aca gca ctg cgt atc aaa aag act     1731
Tyr Gln Asn Pro Ser Ala Arg Leu Thr Ala Leu Arg Ile Lys Lys Thr
480             485             490 ttg acc aaa att gat aat tcc ctc gac aaa ttg aaa act gac tgt tga     1779
Leu Thr Lys Ile Asp Asn Ser Leu Asp Lys Leu Lys Thr Asp Cys
495             500             505 catttcata gtgtcaagaa ggaagatttg acgttgttgt cattgtccag ctgggaccta    1839
atgctggcct gactggttgt cagaatggaa tccatctgtc tccctcccca aatggctgct    1899
ttgacaaggc agacgtcgta cccagccatg tgttggggag acatcaaaac cacccctaacc   1959 tcgctcgatg actgtgaact gggcattttca cgaactgttc acactgcaga gactaatgtt   2019
ggacagacac tgttgcaaag gtagggactg gaggaacaca gagaaatcct aaaagagatc    2079
tgggcattaa gtcagtggct ttgcatagct ttcacaagtc tcctagacac tccccacggg    2139
```

```
aaactcaagg aggtggtgaa tttttaatca gcaatattgc ctgtgcttct cttctttatt    2199
gcactaggaa ttctttgcat tccttacttg cactgttact cttaatttta aagacccaac    2259
ttgccaaaat gttggctgcg tactccactg gtctgtcttt ggataatagg aattcaattt    2319
ggcaaaacaa aatgtaatgt cagactttgc tgcattttac acatgtgctg atgtttacaa    2379
tgatgccgaa cattaggaat tgtttataca caactttgca aattatttat tacttgtgca    2439
cttagtagtt tttacaaaac tgctttgtgc atatgttaaa gcttattttt atgtggtctt    2499
atgattttat tacagaaatg ttttaacac tatactctaa aatggacatt ttcttttatt      2559
atcagttaaa atcacatttt aagtgcttca catttgtatg tgtgtagact gtaacttttt    2619
ttcagttcat atgcagaacg tatttagcca ttacccacgt gacaccaccg aatatattac    2679
tgatttagaa gcaaagattt cagtagaatt ttagtcctga acgctacggg gaaaatgcat    2739
tttcttcaga attatccatt acgtgcattt aaactctgcc agaaaaaaat aactattttg    2799
ttttaatcta cttttgtat ttagtagtta tttgtataaa ttaaataaac tgttttcaag     2859
tcaaaaaaaa aaaaaaaaaa aa                                              2881
```

<210> SEQ ID NO 4
<211> LENGTH: 509
<212> TYPE: PRT
<213> ORGANISM: Homo sapiens

<400> SEQUENCE: 4

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240
```

```
Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
                260                 265                 270

Arg His Ser Ser Thr Gln Leu Trp Leu Ile Thr His Tyr His Glu Met
                275                 280                 285

Gly Ser Leu Tyr Asp Tyr Leu Gln Leu Thr Thr Leu Asp Thr Val Ser
                290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
                340                 345                 350

Ala Asp Leu Gly Leu Ala Val Met His Ser Gln Ser Thr Asn Gln Leu
                355                 360                 365

Asp Val Gly Asn Asn Pro Arg Val Gly Thr Lys Arg Tyr Met Ala Pro
                370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
                435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505
```